United States Patent [19]
Strandberg, Jr. et al.

[11] Patent Number: 5,072,691
[45] Date of Patent: Dec. 17, 1991

[54] APPARATUS FOR MONITORING SIZE ENCAPSULATION OF YARN ON A SLASHER

[76] Inventors: Charles F. Strandberg, Jr., 202 Longview Rd., High Point, N.C. 27260; Robert C. Strandberg, 1718 Aftonshire Dr., Greensboro, N.C. 27410

[21] Appl. No.: 428,992

[22] Filed: Oct. 30, 1989

[51] Int. Cl.$^5$ .............................................. B06C 11/00
[52] U.S. Cl. ..................................... 118/679; 118/234; 118/249; 118/712; 427/8; 427/9; 427/10; 427/394; 427/428
[58] Field of Search ................. 427/9, 394, 8, 10, 428; 118/712, 234, 249, 679

[56] References Cited

U.S. PATENT DOCUMENTS

| | | | |
|---|---|---|---|
| 3,044,345 | 7/1962 | Schottler | 88/14 |
| 3,582,661 | 6/1978 | Emmasingel | 250/219 |
| 4,634,280 | 1/1987 | Paulson | 356/385 |
| 4,710,396 | 12/1987 | Seydel et al. | 427/8 |
| 4,717,870 | 1/1988 | Vuncannon | 118/712 |
| 4,738,866 | 4/1988 | Conklin et al. | 427/10 |
| 4,812,043 | 3/1989 | Vanstaen | 356/385 |
| 4,948,260 | 8/1990 | Felix et al. | 356/429 |

OTHER PUBLICATIONS

"Yarn Hairiness" by A. Barella in *Textile Progress*, Vol. 13, No. 1, Copyright 1983.
"Yarn Evenness" The Textile Institute, *Textile Progress*, Vol. 14, No. 3/4, Copyright 1986.

*Primary Examiner*—Janyce Bell

[57] ABSTRACT

A method for quantifying size encapsulation of yarn on a slasher comprising measuring the hairiness of yarn entering a slasher prior to the application of size to the yarn, measuring the hairiness of the yarn leaving the slasher and solving the equation:

$$\text{Size Encapsulation} = 360\left(1 - \frac{\text{Hairs at Delivery}}{\text{Hairs at Entry}}\right) \text{degrees}.$$

Apparatus for quantifying the size encapsulation of yarn on a slasher comprises an entry hairiness sensor positioned at the entry side of a slasher, a delivery hairiness sensor positioned at the delivery side of the slasher, the entry and delivery sensors producing signals proportional to the hairiness of the yarn at the entry and delivery sides of the slasher respectively, and a computer for solving the above indicated equation and producing an output signal representative of size encapsulation.

7 Claims, 2 Drawing Sheets

APPARATUS FOR MONITORING SIZE ENCAPSULATION OF YARN ON A SLASHER

FIELD OF THE INVENTION

The invention relates to a method and apparatus for monitoring size encapsulation of yarn on a slasher.

BACKGROUND OF THE INVENTION

Size encapsulation is a measure of the degree that a starch film covers the surface of the yarn making up a warp preparatory to weaving.

The sizing machine or slasher utilizes a hot liquid starch bath into which several thousand individual strands or ends of yarn which make up the warp are immersed. After immersion, excess liquid is squeezed out by passing the warp between tightly compressed squeeze rolls. The warp is then passed over several sets of steam heated drying cylinders which evaporate most of the water. An even dispersion of solid starch is left on the yarn in the form of a coating. The starch penetrates the soft yarn, and this helps to keep it from breaking off. Size encapsulation is expressed in degrees from 0 to 360 as an average measure of coverage around the yarn.

Very fine hairs protrude out of the surface of spun yarn before it is sized. One of the main objects of sizing is to bind these hairs to the yarn and cover both with the smooth size film to protect the bundle from the abrasive forces of the loom where the warp will be woven into cloth.

After the warp is dried, adjacent ends or strands may be stuck together by excess size. The adjacent ends are separated by pulling them alternately over and under round bars which extend through the entire warp. During this process, some of the size actually covering the hairs breaks off and the hairs once again protrude outward.

The degree of size encapsulation around each yarn in the warp has always played an important role in reducing loom stops due to warp end breaks. This importance has increased in recent years as a consequence of increasing loom speeds made possible by the use of air instead of a projectile or shuttle to propel the filling yarn through the shed or opening between alternate ends or strands of yarn in the warp.

When lots of hairs protrude off the yarn making up the warp, they impede the air blast and, if sufficiently severe, cause the filling stop motion on the loom to be activated.

This effect was discovered in the mills three years ago, which prompted us to furnish moisture sensors between drying sections on the slasher to assure the optimum amount of moisture in the yarn at the moment it contacts a hot drying cylinder of the final dryer. Our moisture controls are being used now to regulate the steam pressure on the first dryers to achieve this objective.

In connection with this effort to maximize the degree of size encapsulation, we have developed a means of monitoring it on the slasher while the warp is being sized. Not only can the effect of moisture in the warp between drying sections upon size encapsulation be observed and maximized during processing, but other variables can also be adjusted to maximize size encapsulation. These include the moisture in the yarn, the temperature of the liquid size, the temperatures of the drying cylinders, squeeze roll pressure, and tension in the yarn as adjacent ends are separated.

The means consists of two photoelectric optical sensors which convert the passage of hairs on the yarn to a proportional voltage.

One of the sensors is used on one sample yarn at the entry into the sizing process and one is used on a sample yarn at the delivery end of the process.

Since the hairs protrude outward when parts of the size film are lost, the number of hairs remaining compared with the number of hairs on the unsized yarn is a measure of the lack of degree of size encapsulation.

Therefore, $$\text{Size Encapsulation} = 360\left(1 - \frac{\text{Hairs at Delivery}}{\text{Hairs at Entry}}\right) \text{degrees.}$$

Since the warp is stretched by varying percentages depending upon fiber makeup, each unit of yarn length at entry is stretched out to a correspondingly longer length at delivery. No compensation for stretch is necessary, because the output voltage from the sensors is proportional to the number of hairs passing through the sensors per unit of time. By this means, the number of hairs on a unit length of yarn at entry is compared with the number of hairs on the same unit length stretched at delivery.

SUMMARY OF THE INVENTION

The invention relates to a method and apparatus for quantifying size encapsulation of yarn on a slasher by sensing the hairiness of the yarn at the entry end of the slasher, prior to sizing the yarn, and again sensing the hairiness of the yarn at the delivery end of the slasher and solving the equation:

$$\text{Size Encapsulation} = 360\left(1 - \frac{\text{Hairs at Delivery}}{\text{Hairs at Entry}}\right) \text{degrees.} \tag{1}$$

In a preferred embodiment of the invention the hairiness of the yarn at the entry end and at the delivery end of the slasher is measured by entry and delivery photoelectric sensors which sense the hairs projecting outwardly from the body of the yarn and produce an electrical signal which is proportional to the number of hairs projecting from the yarn. The electrical signals produced by the entry and delivery sensors are fed into a computer which solves equation (1) above.

For a perfectly sized yarn, the yarn will be perfectly encapsulated and no hairs will project outwardly from the yarn. The delivery hairiness sensor will detect zero hairs therefore the solution of equation (1) will result in size encapsulation equal to 360 degrees.

If the slasher would fail to size the yarn, the hairiness of the yarn sensed at entry and at delivery would be equal therefore the solution of equation (1) would result in size encapsulation equal to zero degrees.

Neither of the above mentioned extremes are normal, therefore it is an object of the invention to monitor size encapsulation of yarn on the slasher in order that various controls may be adjusted to optimize the degree of size encapsulation.

It is within the scope of the invention that the electrical signal produced by the entry and delivery hairiness sensors may be an analog signal proportional to yarn hairiness or it may be a signal corresponding to a count of the hairs projecting from the yarn.

One hairiness sensor which is adapted for use in this invention and which is a component of the invention comprises a light source emitting rays of light first optical means for collecting rays of light from the light source and converging the collected rays of light in a beam toward a focal point, second optical means located on the opposite side of the focal point from the first optical means for collecting the beam of light emerging from the focal point and converging same along a converging light path, the main core of the yarn sample being located beyond the focal point from the first optical means and extending adjacent and transversely to the light beam emerging from the focal point, the main core being substantially contiguous to and outside of the emerging beam so that hairs projecting from the core on the side of the core nearest the emerging beam intersect the emerging beam and produce a variation in light collected by the second optical means which is proportional to the magnitude of yarn hairiness, photoelectric means positioned in the converging path of light from the second optical means for producing an a-c voltage signal which is proportional to the hairiness of the yarn sample, an audio-frequency amplifier which amplifies the a-c voltage signal from the photoelectric means, a rectifier connected to the amplifier which rectifies the amplified a-c voltage signal from the amplifier, an output load resistor, and a potentiometer having a resistor connected in series circuit with the rectifier, the potentiometer having an adjustable tap which is connected in series circuit with the output load resistor for adjusting the d-c voltage across the load resistor to any desired value that is proportional to yarn hairiness.

With the foregoing objects and features in view and each other objects and features as may become apparent as this specification proceeds, the invention will be understood from the following description taken in conjunction with the accompanying drawings wherein like characters of reference are used to designate like parts.

DETAILED DESCRIPTION OF THE INVENTION

Figure 1:
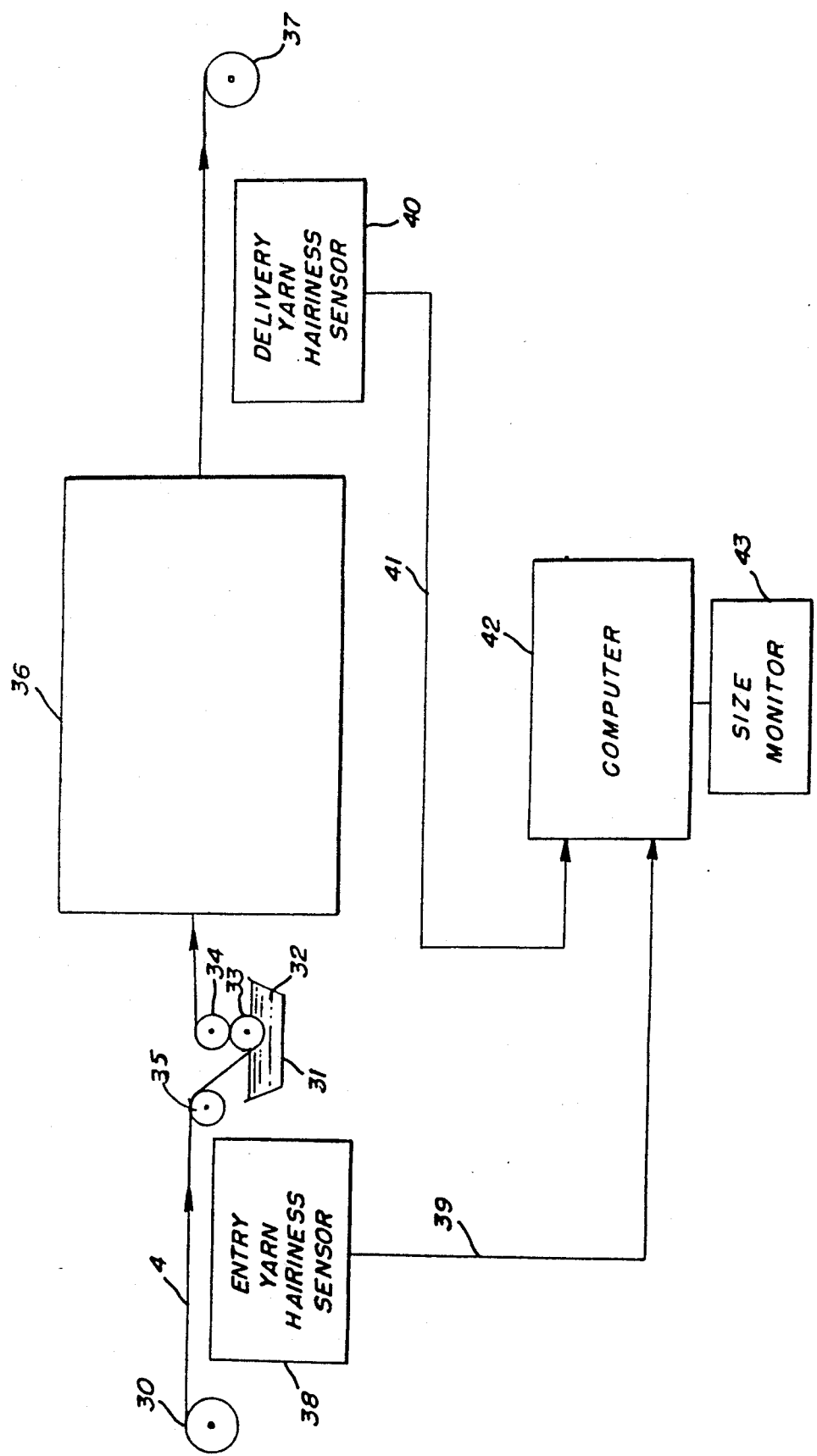
FIG. 1 is a simplified diagram of a typical slasher equipped with the invention.

FIG. 1 shows a diagrammatic view of a simplified typical slasher equipped with the present invention. A warp beam 30 supplies a sheet of warp threads 4 over a guide roll 35 to a size box 31 which is supplied with liquid size 32 to a predetermined level. In the size box 31 the warp sheet 4 is passed under the bottom roll 33 of a pair of squeeze rolls 33 and 34 and it then passes between the upper roll 34 and the bottom roll 33 where pressure is applied to squeeze excess size from the warp sheet. The warp sheet 4 then passes from the upper squeeze roll 34 onto the drying cylinders (not shown) of a drying section 36 to evaporate the water from the liquid size solution to a desired moisture content. The dried warp sheet 4 upon leaving the dryer section 36 passes to the loom beam 37 where it is wound upon the loom beam.

There are many variations of the simplified typical slasher illustrated in FIG. 1 in present use. Most slashers include condition sensors of various kinds for controlling the pressure exerted by the squeeze rolls 33 and 34, for controlling the temperature of the drying cylinders (not shown) in the drying section 36 and for controlling the speed and tension of the warp sheet traveling through the slasher, to mention only some of the known controls used in connection with slashers in current use.

It is not the intent to limit the use of the size encapsulation monitor of the present invention to use with the simplified typical slasher illustrated in FIG. 1, since the size encapsulation monitor may be used in conjunction with slashers of various makes to monitor the degree of size encapsulation of the yarn as it leaves the slasher.

The size encapsulation monitor of the present invention includes an entry yarn hairiness sensor 38 located between the warp beam 30 and the size box 31 and a delivery yarn hairiness sensor 40 located at the delivery side of the drying section 36 near the loom beam 37.

Electric signals generated by the entry and delivery yarn hairiness sensors are supplied over lines 39 and 41 respectively to computer 42 which solves the equation:

$$\text{Size Encapsulation} = 360 \left( 1 - \frac{\text{Hairs at Delivery}}{\text{Hairs at Entry}} \right) \text{degrees.}$$

Size encapsulation in degrees is displayed on the size monitor display 43.

Figure 3:
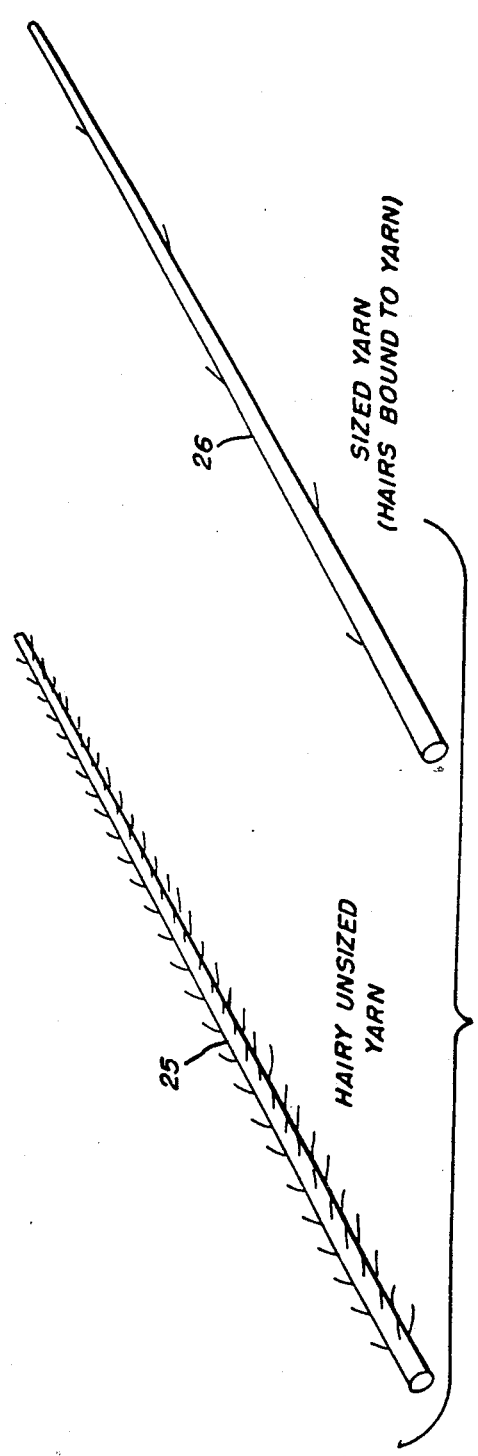
FIG. 3 is a perspective view showing a comparison of the hairiness of unsized and sized yarn.

FIG. 3 illustrates a section 25 of a hairy unsized yarn and a section 26 of a sized yarn which has the hairs bound to the yarn by the size. Even though sizing encapsulates many of the hairs present in unsized yarn, there will still be some hairs protruding from the yarn when the yarn leaves the drying section 36. Various controls may be actuated in response to the size encapsulation signal produced by the computer 42 in order to maintain the maximum possible degree of size encapsulation.

Figure 2:
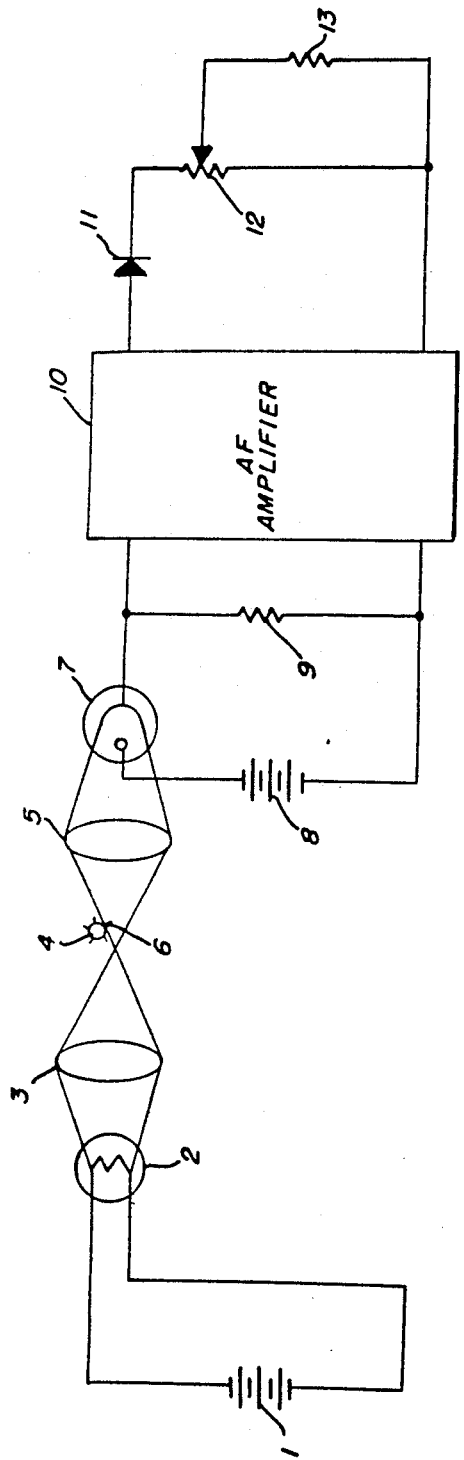
FIG. 2 is a schematic diagram of one of the yarn hairiness sensors used in the invention showing photo electric and optical sensing means.

A yarn hairiness sensor found to be suitable for the entry and delivery yarn sensors 38 and 49 shown in FIG. 1 is illustrated in FIG. 2. The light source 2 contains a spring-wound filament and is powered by a pure d-c source 1. The sample yarn 4 is located immediately outside the narrow slit of light 6 which is before its focal point at the position of the yarn. This location for the sample yarn keeps it outside the field of view but keeps its hair protrusion in the field of view.

The magnitude of yarn hairiness produces a proportional variation in the light projected on the photo diode 7, thus causing its conductance to vary accordingly. This a-c voltage, proportional to yarn hairiness, is developed across a load resistor 9, which is connected to the input of a conventional audio-frequency amplifier 10. After amplification, the resultant proportional voltage is rectified by rectifier 11 and applied across a potentiometer 12 which is used to adjust the output voltage to any desired value that is proportional to yarn hairiness.

While the above described hairiness sensor was developed by us and is a component of the present invention, it is not intended that the invention be limited to the use of the hairiness sensor illustrated in FIG. 2 since other hairiness sensors may be substituted.

Yarn hairiness is discussed under the title "Yarn Hairiness" by A. Barella in Textile Progress, Vol. 13, No. 1, Copyright 1983 by the Textile Institute. Various methods and apparatus for the determination of hairiness are discussed by A. Barella on pages 2-14 of the aforesaid publication.

An apparatus for counting loose fiber ends that may exist on textile threads after spinning is disclosed in U.S. Pat. No. 3,044,345, issued July 17, 1962 to Helmut Schottler.

One yarn hairiness monitor presently in commercial use is the Shirley Yarn Hairiness Meter described on page 8 and illustrated on page 9 of Textile Progress, Vol. 13, No. 1.

Whether the yarn hairiness sensor utilized in the system illustrated in FIG. 1 of the drawing is of the type which produces an analog output signal proportional to yarn hairiness or whether it is of the type which produces a digital output signal representative of a count of the fiber ends projecting outwardly from the yarn counted over some useful length of the yarn is not a limiting factor with respect to the system shown in FIG. 1 since both types of hairiness sensors may be used.

When the hairs are actually counted over a useful length of yarn at entry, they must be counted over the stretched length at delivery. This can be achieved by the use of a tachometer at entry to gate the hairs sensed at entry and delivery to their respective counters.

The term "hairiness" as used in the specification and claims of this patent application refers to the number of loose fiber ends or loops protruding outwardly from a yarn strand over a useful length of the yarn. The loose fiber ends or loops will project from any direction throughout the 360 degree circumference of the yarn. While a useful sampling of the hairiness of the yarn may be taken from only one side of the yarn, as is done by the hairiness sensor shown in FIG. 2, greater accuracy may be obtained by the use of multiple light beams and photocells arranged about the circumference of the yarn so that the hairs projecting in all directions from the yarn may be included in the measurement. The sensor would then have means (not shown) for combining the signals from each of the photocells to produce a combined signal proportional to the hairs projecting from the entire 360° circumference of the yarn.

A feature of this invention is that the delivery yarn sensor 40 may be mounted on a slide bar or other support for movement transversely to the warp sheet as it is being wound on the loom beam. By moving the delivery yarn sensor 40 back and forth transversely with respect to the warp threads, the evenness of size encapsulation of the yarn threads across the entire warp sheet may be tested.

The term slasher as used herein is a term commonly used by the textile industry in the United States with respect to textile sizing machines. In Europe and in some other areas the textile industry more commonly applies the term sizing machine with respect to the same apparatus to which the term slasher is applied in the United States. It is not intended by the use of the term slasher in this application to distinguish from the same apparatus known elsewhere as a sizing machine.

While in the foregoing there has been described and shown a preferred embodiment of the invention, various modifications and equivalents may be resorted to within the spirit and scope of the invention as claimed.

We claim:

1. Apparatus for quantifying size encapsulation of yarn on a slasher comprising:
   a. an entry hairiness sensor positioned at the entry side of the slasher prior to size application of the yarn for producing a signal proportional to the hairiness of the yarn before it is sized,
   b. a delivery hairiness sensor positioned a the delivery side of a slasher for producing a signal proportional to the hairiness of the yarn after the yarn has been sized in the slasher, and
   c. a mathematical equation solving computer responsive to the signals from the entry and delivery hairiness sensors for solving the equation:

$$\text{Size Encapsulation} = 360 \left( 1 - \frac{\text{Hairs at Delivery}}{\text{Hairs at Entry}} \right) \text{degrees},$$

whereby the degree of size encapsulation of the yarn is determined by said computer as the yarn exits the slasher.

2. The apparatus set forth in claim 1 wherein said entry hairiness sensor and said delivery hairiness sensor are photoelectric sensors which produce electrical output signals proportional to the hairs projecting from the yarn at the entry and delivery sides of the slasher respectively.

3. Yarn hairiness sensor apparatus for monitoring the hairiness of a moving yarn sample which has an elongated main fiber core and loose fibers, known as hairs, projecting outwardly from said core in combination with a means to size yarn, said sizing means including a yarn entry side and a yarn delivery side, and yarn coating and drying facilities comprising:
   a. a first yarn hairiness sensor positioned at the entry side of said sizing means prior to size application of the yarn for producing a first electrical signal proportional to the hairiness of the yarn before it is sized,
   b. a second yarn hairiness sensor positioned at the delivery side of said sizing means for producing a second electrical signal proportional to the hairiness of the yarn after the yarn passes through said sizing and drying facilities, and
   c. a mathematical equation solving computer responsive to said first and said second electrical signals whereby said computer will determine the degree of size encapsulation of said yarn sample as said yarn sample exits said sizing means.

4. Apparatus for quantifying size encapsulation of yarn on a means to size yarn as the yarn passes therethrough comprising:
   a. an entry hairiness sensor positioned at the entry side of said sizing means for sensing yarn hairiness prior to sizing,
   b. a delivery hairiness sensor positioned at the delivery side of said sizing means for sensing the yarn hairiness subsequent to sizing, and
   c. a mathematical equation solving computer in communication with said entry and said delivery hairiness sensors whereby the degree of size encapsulation is determined by said computer as the yarn exits said sizing means.

5. Apparatus as claimed in claim 4 wherein said entry hairiness sensor comprises a signal producing sensor.

6. Apparatus as claimed in claim 4 wherein said delivery hairiness comprises a signal producing sensor.

7. Apparatus as claimed in claim 4 wherein said computer comprises a processor for solving the equation:

$$\text{Size Encapsulation} = 360 \left(1 - \frac{\text{Hairs at Delivery}}{\text{Hairs at Entry}}\right) \text{degrees.}$$

* * * * *